United States Patent [19]

Junker et al.

[11] Patent Number: 5,161,413
[45] Date of Patent: Nov. 10, 1992

[54] APPARATUS AND METHOD FOR GUIDED INSPECTION OF AN OBJECT

[75] Inventors: Warren R. Junker, Monroeville; Michael J. Metala, Murrysville; William G. Clark, Jr., Murrysville Boro, all of Pa.

[73] Assignee: Westinghouse Electric Corp., Pittsburgh, Pa.

[21] Appl. No.: 666,323

[22] Filed: Mar. 8, 1991

[51] Int. Cl.⁵ .................. G01N 29/10; G01N 29/26
[52] U.S. Cl. ................................................. 73/634
[58] Field of Search ............... 73/634, 643, 620, 628, 73/625

[56] References Cited

U.S. PATENT DOCUMENTS

| | | | |
|---|---|---|---|
| 3,553,570 | 1/1971 | Skubiak et al. | 73/634 |
| 4,160,386 | 7/1979 | Jackson et al. | 73/625 |
| 4,167,878 | 9/1979 | Bottcher et al. | 73/601 |
| 4,206,511 | 6/1980 | Ries et al. | 73/625 |
| 4,235,112 | 11/1980 | Kaiser | 73/634 |
| 4,530,243 | 7/1985 | Lund et al. | 73/633 |
| 4,559,825 | 12/1985 | Martens | 73/622 |
| 4,856,337 | 8/1989 | Metala et al. | 73/601 |
| 4,891,986 | 1/1990 | Teagle | 73/634 |

Primary Examiner—John E. Chapman
Assistant Examiner—Rose M. Finley

[57] ABSTRACT

A device and method for guided testing of an object, and in particular, an internal structural component in an object, using non-destructive ultrasonic techniques is provided. A housing containing at least one ultrasonic transducer probe is adapted to be placed directly on the surface of the object to be tested. Eddy current probes are provided in the housing to guide the ultrasonic probe such that the ultrasonic energy will be directed at the appropriate internal structural design component of the object to be inspected. A microcomputer is then used to record the data obtained using ultrasonic signals and the position on the object using the information designed from the eddy current probes.

20 Claims, 4 Drawing Sheets

APPARATUS AND METHOD FOR GUIDED INSPECTION OF AN OBJECT

BACKGROUND OF THE INVENTION

1. Field of the Invention

This invention relates generally to an apparatus and method for non-destructive, guided inspection of an object. More particularly, the invention is directed towards ultrasonic inspection of internal structural features using eddy current probes to guide the ultrasonic inspection.

2. Background Information and Description of the Prior Art

This invention relates generally to non-destructive examination of internal structural components of an object. The device is specifically directed towards an apparatus and method for inspecting internal components using ultrasound inspection techniques which are guided by eddy current probes. The eddy current probes detect the location of the internal structure such that the ultrasonic energy will be appropriately directed and the resulting data will be accurately interpreted. The invention is particularly useful for inspection of internal ribs in an aircraft wing or weld seams in piping or welded components of a structure.

Devices for inspecting objects in a non-destructive manner using ultrasonic inspection probes, or eddy current inspection probes have been known. One device and method which discloses the use of a combination of ultrasonic and eddy current probes for inspection of a device is owned by the assignee of the present invention. More specifically, U.S. Pat. No. 4,856,337 discloses an apparatus and method for providing a combined ultrasonic and eddy current inspection of a tube. The device is directed towards inspecting the walls of conduits such as heat exchanger tubes in nuclear steam generators. The eddy current probe is used to inspect the surfaces of the metal walls of the tube and the ultrasonic probe is used to check for internal flaws in the tube walls. A drive train is provided to impart a helical motion to a probe carrier which travels throughout the tube to be inspected.

Another apparatus which discloses use of both ultrasound and eddy current inspection probes is disclosed in U.S. Pat. No. 4,167,878. The device utilizes ultrasonic probes to test for internal flaws and an eddy current device to test for surface flaws. The device is arranged such that the two testing probes have at least approximately a common central axis.

Other devices for inspecting objects for subsurface flaws utilizing sonic transducers have been known, such as the device disclosed in U.S. Pat. No. 4,559,825.

One of the problems which arises in non-destructive industrial testing is that of precisely locating a flaw which has been detected by an ultrasonic transducer device. Typically, an indication that a flaw exists is generated by the ultrasonic transducer but the difficulty arises in detecting the exact location of the defect with respect to the internal structure. U.S. Pat. No. 4,235,112 discloses a laterally movable ultrasound transducer for use in inspecting rail faults. The device includes a pair of ultrasound receiving transducers positioned on either side of a main transmitting transducer. Signals provided by the receiving transducers are compared and the signals are used to determine and control the lateral position of the sensor with respect to the rail being inspected. Another method for determining the position of a measuring sensor or probe was disclosed in U.S. Pat. No. 4,530,243. This method primarily focuses on determining position with respect to a frame by measuring voltage drops across individual bars comprising the frame to determine the relative position of a detected flaw with respect to the bars of the frame.

An ultrasonic inspection system including apparatus and method for tracking and recording a location of an inspection probe was disclosed in U.S. Pat. No. 4,160,386. This device and method includes one or more sources of radiant energy located on a probe which are periodically actuated as the probe is moved about an object being inspected. The radiant energy is detected by receiving devices or microphones located at known points with respect to the area being inspected or with respect to a known reference point such as a weld. As the radiant energy is picked up by the receiving devices, the location of the probe can be determined and recorded.

The above mentioned devices provide apparatus and methods for non-destructive industrial testing utilizing ultrasound and, in some cases, combinations of ultrasound and eddy current devices. As discussed, some methods are also disclosed for locating the position of the probe with respect to a known point to provide a method for determining the location of a detected flaw with reference to that known point. However, these methods are not entirely reliable and, in addition, these devices have not heretofore provided a method for determining where to direct the ultrasonic energy for the inspection. More particularly, it is often necessary to focus the inspection upon a particular internal structural member of an object which is known to be prone to developing cracks, tears or other structural defects. However, if such internal structural components are not visible, there is difficulty in determining where to direct the ultrasonic energy in the course of an inspection. For example, inspection of aircraft wings has become of increasing importance in both commercial and military aviation with respect to aging aircraft. Inspection of the wings is directed primarily towards inspection of the underlying ribs or T-shaped cross sections which provide the structure for the airfoil. This rib is often called a stringer. The area where the stringer joins the surface of the airfoil is often a high stress region and a non-destructive examination of this region is typically included in routine service inspection requirements. It is important to direct an ultrasonic inspection at this region of the wing.

A typical wing panel inspection would first involve locating the ribs or stringers. Conventionally, a special template is placed on the wing surface and the rib location is marked. The template is used along with engineering drawings of the wing to determine the exact location of the ribs. A manual ultrasonic inspection would then be conducted during which the transducer is moved back and forth across the rib region. Although the test is simple in principle, the use of the rib-locating template is very time consuming. In addition, interpretation of test results can be extremely difficult and can be inaccurate because the aircraft wings are often not built in exact conformity with the original engineering drawings. Data interpretation problems also stem from the fact that a crack signal can be masked by a top plate thickness signal. Thus, positioning of the transducer at the rib is critical to developing accurate, reliable data.

Similarly, problems arise in inspecting for cracks and tears along a weld seam in piping or other ducts and conduits. Of particular interest are components which have had the weld crown machined so that it is flush with the base metal as is often the case with welded pipe. To inspect the weld metal and adjacent heat-affected zone, a manual ultrasonic angle beam examination is routinely performed. To assure that the complete weld zone is inspected, the weld region and designated inspection area is outlined in a grid pattern with a marker pen on the surface of the component. However, initially identifying the actual weld location after the crown has been removed is difficult and often requires expensive and time consuming metal etching procedures before the inspection can take place.

There remains a need, therefore, for a device which can be incorporated with ultrasonic inspection probes, and which can provide guidance for the probe to a desired location on an object such that the ultrasonic energy can be directed towards a pre-selected internal structure to be inspected. In addition, there remains a need for a device which can be used to eliminate false discontinuity signals which are generated from internal structures from actual discontinuities representative of internal flaws in the object.

SUMMARY OF THE INVENTION

These and other needs are satisfied by the device and method of the present invention which include an inspection device for inspecting the integrity of an object along a selected internal structure of the object. The invention includes a housing carriage which is movable on the surface of the object along a predetermined path. Typically, the predetermined path will be generally adjacent an internal structural component of the object. An ultrasonic probe transmits ultrasonic energy into the object to generate reflected energy when the transmitted energy impinges upon a discontinuity in the object. The ultrasonic probe is guided by an eddy current guide component which is also disposed in the housing. In a preferred form, an eddy current probe is placed on either side of the ultrasonic probe. The two eddy current probes each generate an electromagnetic field in the object. Disruptions in the field are created at an edge of the underlying structural component of the object. The eddy current probe detects the disruptions in the field and generates an electronic signal when disruptions are detected. The two eddy current probes can be used to detect opposed edges of an internal structural feature such as a rib in an aircraft wing. The two signals generated from the eddy current probes can be used to select the lateral positioning of the ultrasonic probe so that it remains within the desired path as it travels longitudinally along the path during an inspection.

Other structural features can also be detected by the eddy current probes. In some applications, only one eddy current probe is necessary. For example, if one edge of the internal structural feature is relevant, then one eddy current probe could be used to detect the edge of the step.

Associated signal processing components are disclosed which further utilize the eddy current position signals to eliminate false discontinuity signals arising from the ultrasonic energy impinging upon internal structural features rather than defects in the object. A more accurate inspection signal can be obtained if such signals arising from structural features are eliminated.

In accordance with another aspect of the invention, a focusing device is provided with which the ultrasonic probe will concentrate the ultrasonic energy into a beam for direction onto a predetermined portion of the object. This focusing device can also be provided with a scanning device which allows the focused beam to scan back and forth across the lateral width of the inspection path as the housing carriage moves longitudinally along the path. This allows essentially the entire area of the path to be inspected.

The eddy current guide means can also be utilized with other types of probes when it is desired to direct the probe at an internal structural feature which is not visible.

The device can be used with a meter which can be observed by an operator during manual inspection. In that embodiment, the meter indicates when the inspection device is outside the desired path and the operator can correct the position to remain within the path while performing the inspection. Alternatively, the position signals generated by the eddy current probes can be used to remotely control the device to automatically correct the position of the inspection device as it performs the inspection along the path adjacent a selected internal structural component.

DESCRIPTION OF THE PREFERRED EMBODIMENTS

Figure 1:
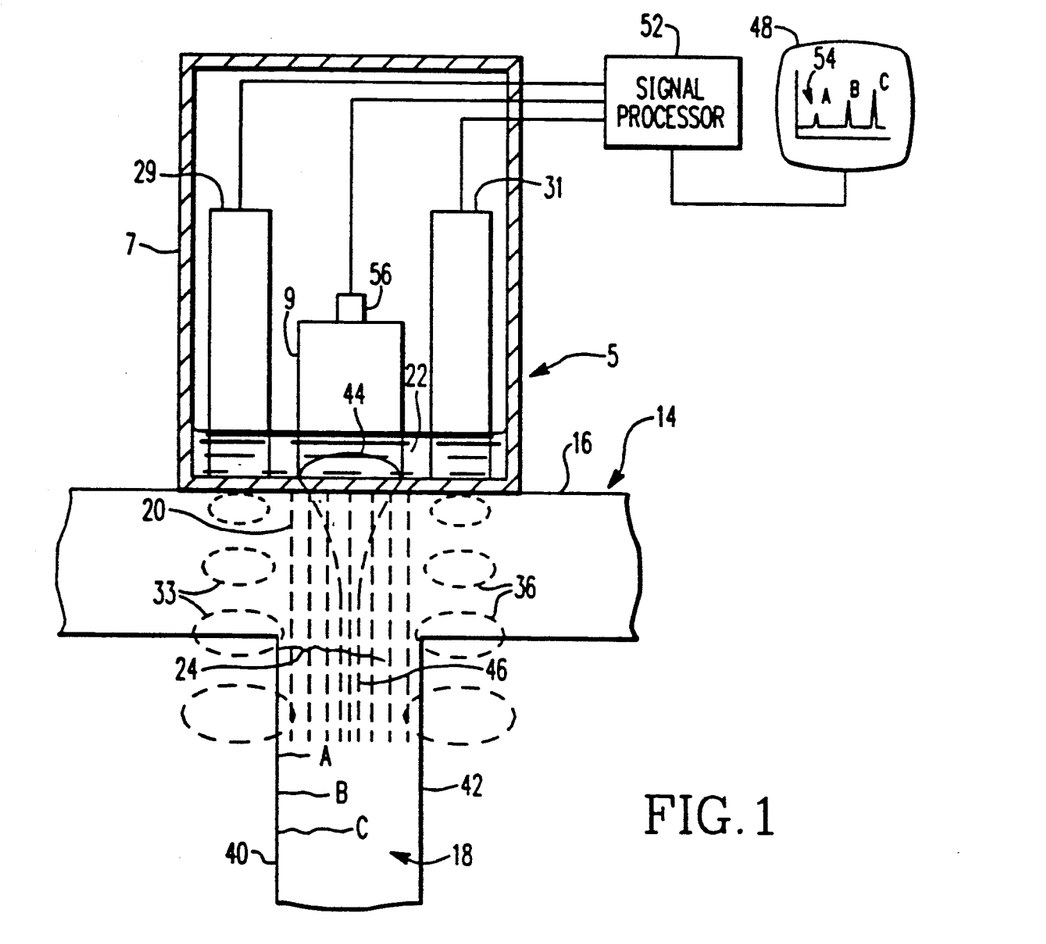
FIG. 1 is a schematic illustration of the eddy current-guided ultrasonic inspection device of the present invention.

Referring to FIG. 1, the inspection device 5 of the present invention is enclosed within housing 7. The inspection device includes ultrasonic transducer probe 9. The transducer probe 9 has a source which will emit ultrasonic energy in a manner which is understood by those skilled in the art. Housing 7 would also contain water 22 schematically illustrated in FIG. 1 through which sound waves can propagate for coupling.

In the exemplary embodiment of FIG. 1, the device 5 is to be used to inspect object 14. More particularly, the area of interest is the perpendicular component which is an internal structure 18 of object 14. The device 5 is placed on surface 16 and ultrasonic energy shown schematically as waves 20 are directed towards object 14. The ultrasonic energy 20 is emitted by probe 9 towards structural component 18. If there is a flaw such as crack 24 in component 18 echoes will be generated and will be received by a transducer included within probe 9. Probe 9 will convert these echoes into electrical signals and these electrical signals will be provided as the information bearing input signals to an associated signal processing device 52.

In order to guide ultrasonic transducer probe 9 to the correct location such that the ultrasonic energy can be transmitted towards component 18, an eddy current guide system is provided. In the embodiment shown in FIG. 1, two eddy current probes 29 and 31 are provided on opposite sides of ultrasonic transducer probe 9. The eddy current probes 29 and 31 may be either single coil eddy current probes or dual coil eddy current probes as may be desired in the particular application. Eddy current probes 29 and 31 each contain a source which produces the electromagnetic field which is schematically indicated by flux lines 33 in the case of eddy current probe 29 and by flux lines 36 with respect to eddy current probe 31. The eddy current probes such as probe 29 are capable of detecting disruptions in field 33 which are in turn converted into electrical signals representative of the field disruptions. These signals are sent to the associated signal processing unit 52.

As would be readily understood by those skilled in the art, disruptions in field 33 occur at an edge such as edge 40 on component 18. These disruptions are detected by eddy current probe 29. Similarly, edge 42 can be detected when disruptions in field 35 are created. These disruptions would be detected by eddy current probe 31. As soon as a disruption is detected, it is known that the eddy current probe 29, for example, is positioned over the edge 40. In this way, information can be derived about the position of housing 7 and in turn ultrasonic transducer probe 9 with respect to component 18. Signals produced by eddy current probes 29 and 31 can give a ready indication of whether the ultrasonic transducer probe 9 is at an appropriate position such that the ultrasonic energy will be directed at component 18.

For example, if the device 5 is too far to the right in FIG. 1, eddy current probe 31 will provide an "off" signal indicating that the device is not ready. The opposite probe 29 may still provide an "on" signal indicating that the left side is properly positioned. Thus, in a manual device application, the operator would know to move the device 5 to the left. Alternatively, if the device 5 is too far to the left, an "off" signal from probe 29 would be presented indicating that the left side of the device is not appropriately lined up. The details of the signal processing steps for these signals are described in further detail hereinafter.

In accordance with another aspect of the invention, ultrasonic probe 9 may be provided with a spherical contour 44 which results in a focused beam 46 of ultrasound energy. The beam 46 is directed at a more concentrated portion of component 18. This aspect of the invention is schematically illustrated by the concentrated waves 46 directed at component 18.

In addition, a motor and associated scanning device 56 can be provided on probe member 9. This scanning member 56 would serve to direct the beam in preferably a sinusoidal pattern across component 18. In this way, the entire width of component 18 can be inspected as the housing 7 is passed longitudinally across component 18. The spherical contour and scanning device 56 are components which are available to those skilled in the art.

Figure 2:
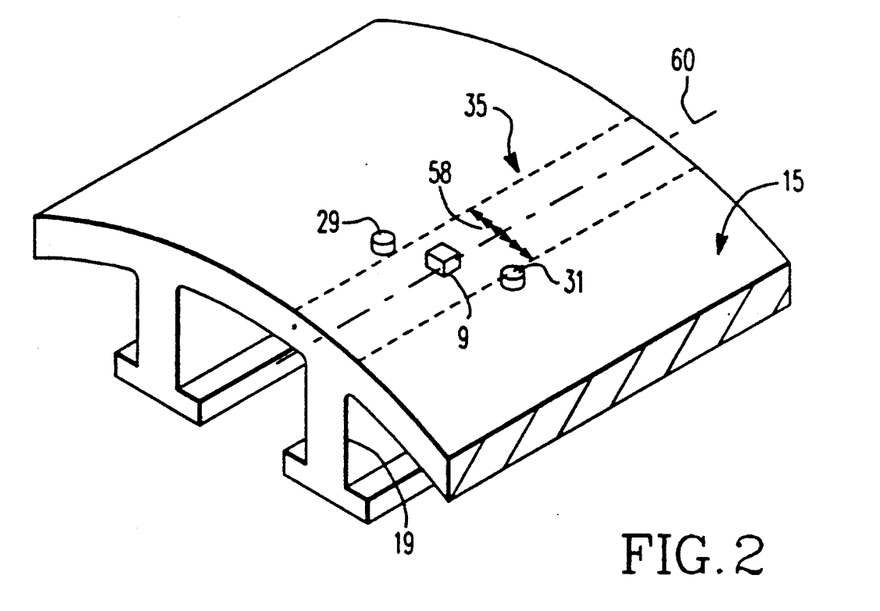
FIG. 2 is a schematic isometric illustration of one embodiment of the device using a scanning ultrasonic transducer probe over the rib of an aircraft wing.

This can be better understood with reference to FIG. 2 which is a schematic isometric illustration of a selected portion such as rib 19 of an aircraft wing 15 to be inspected. As the inspection is to be conducted of the rib 19, the ultrasonic probe 9 should remain on path 35. Eddy current probes 29 and 31 are used to maintain probe 9 within the limits of the path 35. Ultrasonic transducer probe 9 has the scanning device (not visible) associated therewith. Ultrasonic scanning probe 9 moves back and forth such that the energy beam passes back and forth laterally as shown by arrows 58 in FIG. 2. As the housing containing ultrasonic probe 9 passes along longitudinal axis 60 of component 19 the ultrasonic probe 9 scans back and forth across the width of path 35 and in this way the entire underlying component 19 is inspected.

It is also noted that an ultrasonic transducer display unit 48 can be provided with the system in connection with signal processor 52. (FIG. 1). The display unit will provide a spectrum indicative of cracks or other irregularities in the object 14. For example, defects such as are marked with the letters A, B and C in FIG. 1 will result in corresponding peaks in curve 54 shown in the display unit 48. The method of generating the display of unit 48 would be readily understood by those skilled in the art.

Figure 3:
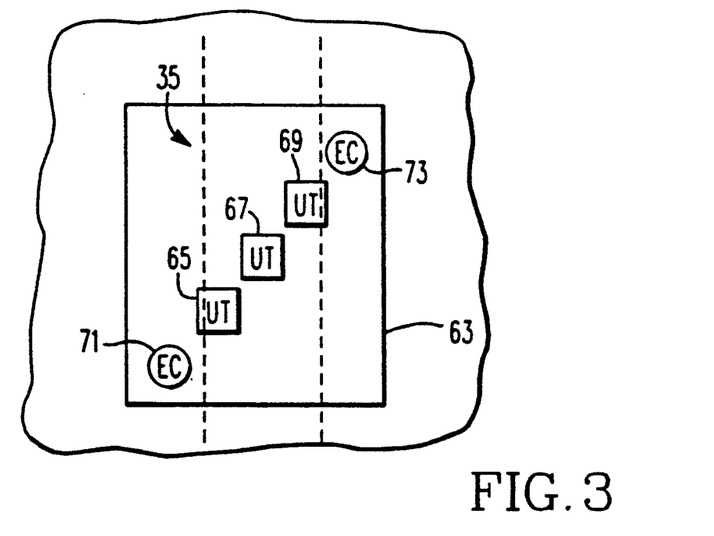
FIG. 3 is a schematic illustration of another embodiment of the device utilizing multiple ultrasonic transducer probes.

In accordance with yet another aspect of the invention which is shown in FIG. 3, multiple ultrasonic transducer probes can be provided in housing 7. More specifically, transducer probes 65, 67 and 69 are provided instead of a scanning device to ensure that the entire width of path 35 is covered for the inspection.

Figure 4:
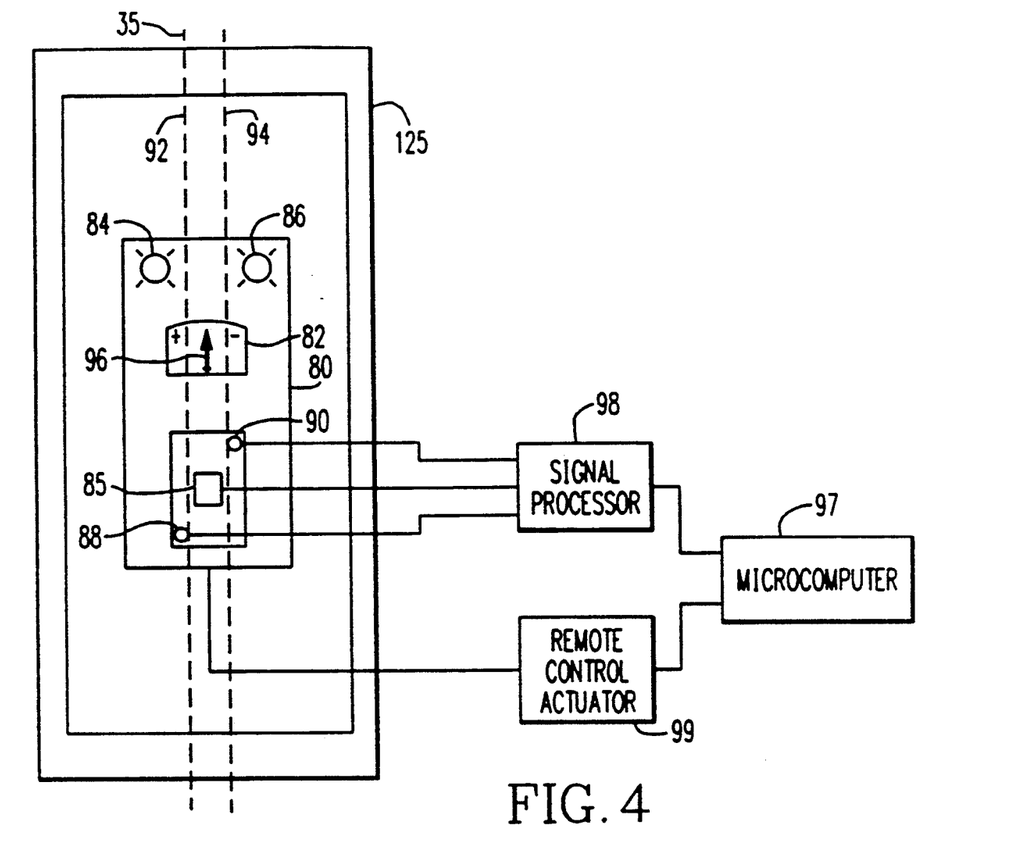
FIG. 4 is a schematic illustration of the frame encoder and meter used with the device of the present invention.

Referring now to FIG. 4, housing 80 may include meter 82 which provides a visual indication of the position of housing 80 with reference to path 35 and underlying component 18 (not visible in FIG. 4). In addition to meter 82, indicator lights such as lights 84 and 86 can also be provided to indicate whether the housing 80 and, more particularly, whether ultrasonic transducer probe 85, is aligned properly with respect to component 18. As discussed above, eddy current probes 88 and 90 can be provided on either side of ultrasonic transducer probe 85. When the housing is moved towards edge 92 of path 35 eddy current probe 88 will detect this edge and a resultant signal will be suitably transmitted to indicator light 84. The light 84 will come on to indicate that one side is lined up with edge 92. Similarly, edge 94 will be detected by eddy current probe 90 and indicator light 86 will be lit.

Meter 82 provides additional information as to the position of ultrasonic transducer probe 86. As shown in FIG. 4, needle 96 is centered indicating correct positioning. If, however, the needle 96 points towards the positive sign on the left of meter 82 this would indicate that the housing should be moved toward the left in order to line up properly on path 35. If, on the other hand, the needle 96 points towards the minus sign shown in meter 82, then this would indicate that the housing 80 should be moved towards the right to appropriately line the device up on path 35.

If it is desired not to provide a manual inspection device, a microcomputer such as microcomputer 97 shown in FIG. 4 can be suitably programmed to receive digitized signals from an associated signal processor 98 which includes an analog to digital converter. These signals would be generated from the analog signals generated by eddy current probes 29 and 31. The computer 97 is programmed to issue instructions to a suitable remote control device schematically illustrated as 99 which would then automatically take a corrective action by moving the housing 80 towards the right or the left as appropriate.

Figure 5:
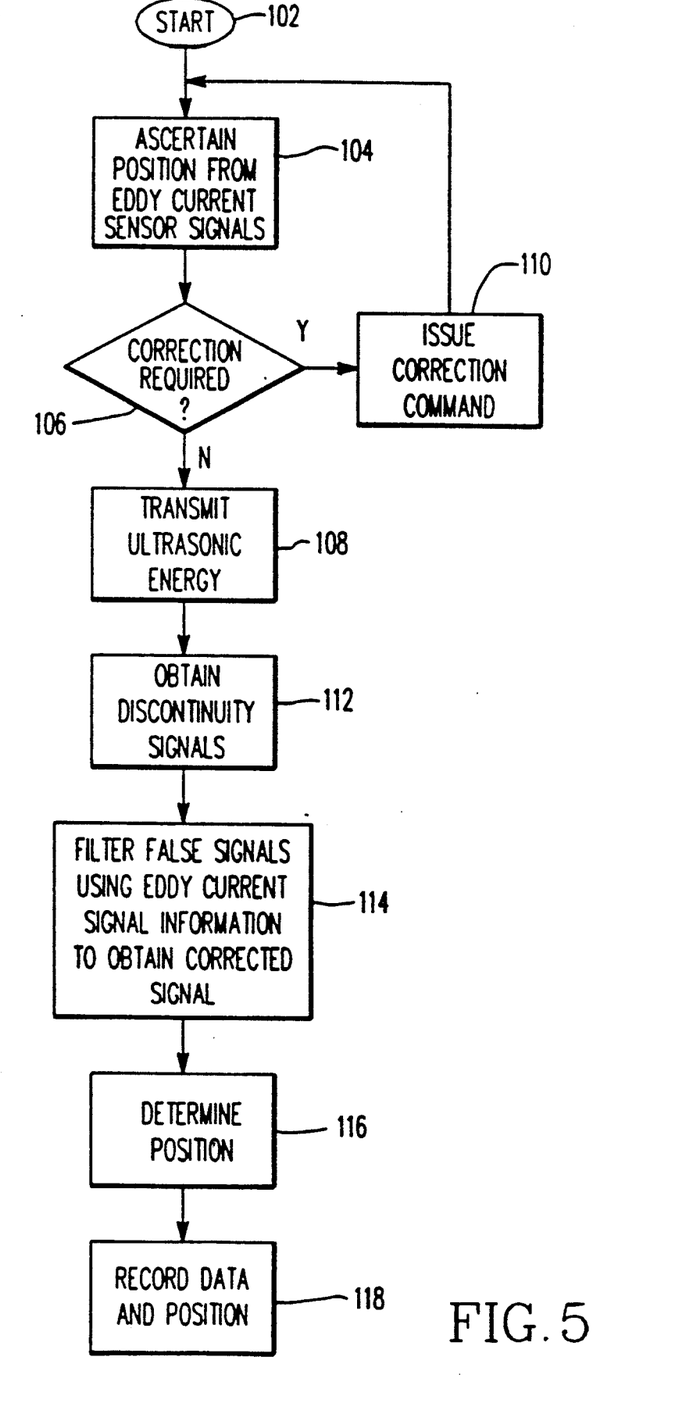
FIG. 5 is a schematic illustration of a portion of a pipe in which the weld seam is to be inspected by the device of the present invention.

As mentioned above, the microcomputer 97 may be additionally programmed to retrieve the information from the ultrasonic probe such as probe 85 in FIG. 4. This aspect of the method of the present invention is shown in the flow chart of FIG. 5. FIG. 5 shows the steps to be followed in a program for conducting an investigation of an object with reference to an internal component within the object in accordance with the present invention. The program is started by an appropriate signal indicating readiness of the system as shown in step 102. As shown in step 104, the position of housing 80 (FIG. 4) must be ascertained by reading the probe signals issued by eddy current probes 88 and 90. The microcomputer is programmed to determined whether a correction is required as shown in step 106. This can be done utilizing a simple interrogation to determine whether both signals from the probes are indicating that the device is on the respective edge such as edges 92 and 94 (FIG. 4), as discussed above. If both signals are reading "on", no correction is required and the program continues to step 108. If a correction is required, an appropriate command will be issued to carry out that corrective action or to instruct an operator to manually take corrective action. This is shown in step 110. After the correct position is ultimately achieved then a signal is generated and issued to ultrasonic transducer probe 85 to transmit ultrasonic energy, as shown in step 108. Ultrasonic energy is reflected at discontinuities in the manner discussed hereinbefore and transducer probe 85 converts these signals into electrical signals which are then sent to the analog-to-digital converter circuitry in signal processor 98 and converted to digital signals readable by the microcomputer 97. The computer is programmed to obtain this discontinuity information from such signals as shown in step 112. This information is first filtered as shown in step 114 to remove any false discontinuity signals which arise as a result of the ultrasonic energy impinging upon edges such as edge 92 of the internal structural component to be inspected. Once a corrected signal is obtained the position from which the discontinuity was reflected is determined, as shown in step 116.

The position can be even more precisely determined with reference to a frame such as frame 125 shown in FIG. 4. Frame 125 is be placed at a known position on the underlying object. The position within the object of the discontinuity can then be determined with reference to the frame using linear acoustic microphones, encoders attached to the device, surface wave triangulation, a ball encoder mounted in the device or other suitable components. After this has been performed, the data is recorded along with an accompanying position as shown in step 128 (FIG. 5).

Figure 6:
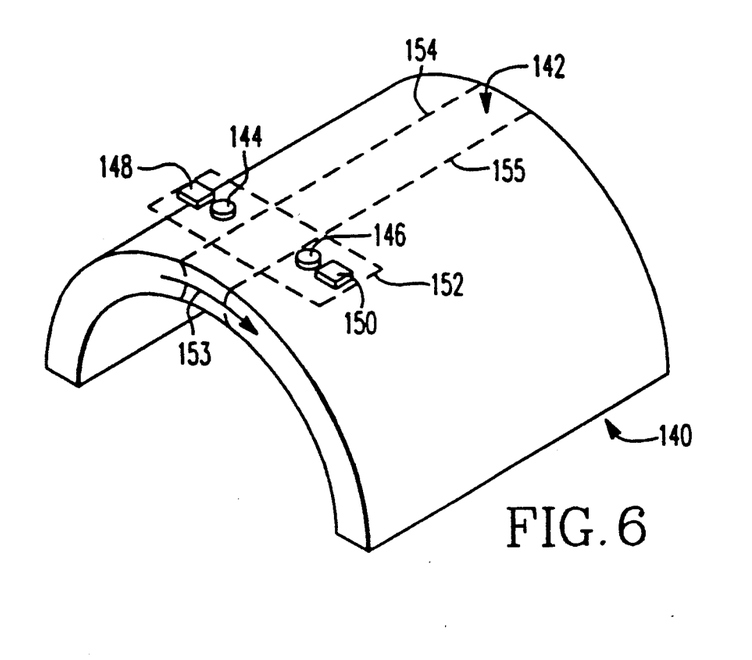
FIG. 6 is a flow chart of the steps undertaken in performing the inspection method of the present invention.

Yet another application of the invention is shown in FIG. 6. A section of pipe 140 has a weld seam 142 which is to be inspected. The path to be followed in the exemplary case of FIG. 6 by the inspection device is contiguous with weld seam 142. In other applications, a broader path may be desired. The weld bead of this weld has been ground flush with the piping in this example. In this embodiment of the device, two eddy current probes 144 and 146 are placed in line and adjacent to two ultrasonic probe devices 148 and 150. Eddy current probes 144 and 146 are separated by a predetermined distance corresponding to the width of weld seam 142 and if desired, an additional portion may be added to the inspection zone. Each pair of an eddy current probe and an ultrasonic probe is used to inspect the weld seam 142 and adjacent zone in one direction. More specifically, both eddy current probes 144 and 146 are initially positioned on the base metal straddling the weld seam 142 as shown in FIG. 6. Initially, ultrasonic transducer probe 148 emits ultrasonic energy in the clockwise direction. As the inspection device generally designated 152 is moved in the clockwise direction as shown by arrow 153, the clockwise-aimed ultrasonic probe 148 begins interrogating the weld seam 142. The corresponding eddy current probe 144 moves from side 154 of the seam 142 over the weld metal surface until it senses the base metal pipe material on the opposite side 155. Then, ultrasonic transducer 150 emits ultrasonic waves in the counter-clockwise direction and the device 152 is then moved in the counter-clockwise direction to provide a similar inspection from that direction. This may be performed manually, or by a remote device Other configurations of the eddy current probes and ultrasonic transducers may be used as desired in the particular application.

It should be appreciated that the device and method of the present invention provide a simple method of conducting guided non-destructive testing using an ultrasonic probe and an eddy current probe to guide the ultrasonic probe.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limited as to the scope of the invention which is to be given the full breadth of the appended claims and any and all equivalents thereto.

What is claimed is:

1. An apparatus for inspecting the integrity of an object along a selected internal structural designing feature of said object, comprising:

housing means being movable on a surface of said object along a predetermined path generally adjacent said structural design feature;

ultrasonic probe means disposed in said housing means, said ultrasonic probe means having means for transmitting ultrasonic energy into said object to generated reflected energy when said transmitted energy impinges upon a discontinuity in said object, and transducer means for generating electronic inspection signals when said reflected energy is detected; and eddy current guide mans disposed in said housing means for guiding said ultrasonic probe means along said path, said eddy current guide means having means for generating an electro-magnetic field in said object such that disruptions in said field are generated by said structural design feature of said object, and for detecting said disruptions in said field and for generating electronic position signals when said disruptions are detected said electronic position signals being used by said eddy current guide means to generate a signal for guiding said ultrasonic probe means to maintain said ultrasonic probe means on said path.

2. The apparatus of claim 1 further comprising:

focusing means operatively associated with said ultrasonic probe means for concentrating said transmitted ultrasonic energy into a beam, and said focusing means having means for directing said beam onto a predetermined portion of said object.

3. The apparatus of claim 2 wherein
said housing means has means for moving said housing means longitudinally along said path, and said focusing means also has scanning means for moving said beam in a continuous pattern generally laterally across said path to direct said beam over substantially the entire width of said path.

4. The apparatus of claim 3 wherein
said housing also includes frame means positioned over said housing to frame a section of said object over said path, said frame means having locator means for recording said reflected energy with respect to said frame means to determine a location of a discontinuity in said object with reference to said frame means.

5. The apparatus of claim 1 wherein
said selected structural design feature has two parallel edges, and a center portion; and
said eddy current guide means comprises a pair of eddy current probe means disposed in said housing means on opposite sides of said ultrasonic probe means, a first probe means in said pair detecting disruptions at a first edge of said structural design feature and generating a first position signal representative of said first edge and a second probe means in said pair detecting disruptions at a parallel, second edge of said structural design feature and generating a second position signal representative of said second edge.

6. The apparatus of claim 5 further comprising:
position signal processing means for processing said first and second position signals to determine the location of said guide means with respect to said first and second edges to maintain said ultrasonic probe means on said path.

7. The apparatus of claim 6
said position signal processing means has display means for providing visual indicia based on said generated information of a lateral position of said ultrasonic probe means on said which includes visual display means connected with said signal processing means for providing visual indicia representative of irregularities of said internal structural design feature.

8. The apparatus of claim 6 further comprising:
microcomputer means operatively associated with said ultrasonic probe means and said position signal processing means, said microcomputer means having means for receiving said inspection signals and said position signals and means for storing said signals.

9. The apparatus of claim 8 further comprising:
remote control means operatively associated with said microcomputer means and said housing such that said remote control means maintains said housing on said path based on commands from said microcomputer means.

10. The apparatus of claim 1 wherein
said ultrasonic probe means comprises two ultrasonic probes and said eddy current guide means comprises two eddy current probes, a first probe associated with a first ultrasonic probe means and a second probe associated with a second ultrasonic probe means, and said first and second probes being spaced apart from one another a predetermined distance to encompass a predetermined portion of said object adjacent said internal structural feature.

11. The apparatus of claim 1 further comprising:
inspection signal analyzing means for combining said position signals and said inspection signals, said analyzing means having means for generating a corrected inspection signal by filtering inspection signals generated when said ultrasonic probe means is outside said path to eliminate false discontinuity inspection signals arising when an inspection signal is generated as a result of transmitted energy from said ultrasonic probe means impinging upon said structural design feature.

12. An apparatus for sensing the position of an associated probe means on an object with respect to an internal structural design feature of said object, comprising:
housing means being movable on a surface of said object;
probe means disposed in said housing means such that said probe means is directed at said surface; and
eddy current guide means disposed in said housing means, said guide means having field generating means for generating an electromagnetic field in said object such that a disruption in said field is generated by said internal structural design feature and, said guide means also having means for detecting said disruptions in said field and for generating electronic position signals when said disruptions are detected, said electronic position signals being used by said eddy current guide means to generate a signal for guiding said probe mean to maintain said probe means on a predetermined path with respect to said internal design feature.

13. The apparatus of claim 12 in combination with said internal structural design feature having two parallel edges and a center portion between said edges, wherein
said eddy current guide means comprises a first eddy current probe means for detecting disruptions occurring at a first edge of said internal structural design feature and generating a first position signal representative of said first edge, and second eddy current probe means for detecting disruptions at a second, parallel edge of said internal structural design feature and generating second position signal representative of said second edge.

14. The apparatus of claim 13 further comprising:
position signal processing means for processing said first and second position signals to determine the location of said guide means with respect to said first and second edges.

15. The apparatus of claim 14 further comprising:
remote control means operatively associated with said housing means and movable in response to said first and second position signals for maintaining said probe means in a predetermined position with respect to said internal structural design feature of said object.

16. The apparatus of claim 14 wherein
said housing means also includes frame means positioned over said housing means to frame a predetermined portion of said object, said frame means having locator means for determining positions on said object with respect to said frame.

17. The apparatus of claim 13 wherein said probe means comprises a plurality of probe members disposed in said housing means such that said probe members are spaced laterally across said path to inspect substantially the entire width of said path.

18. A method of inspecting an object along a preselected path on said object adjacent to an internal structural design feature of said object, including the steps of:
   providing an inspection housing adapted to be placed on a surface of said object on said path, including an ultrasonic probe means and an associated eddy current guide means in said housing;
   operating said eddy current guide means to generate an electromagnetic field in said object adjacent said structural design feature to locate said structural design feature by detecting disruptions in said field occurring at said structural design feature;
   converting aid detected disruptions into position signals usable to ascertain the position of said housing on said path;
   operating said ultrasonic probe means to transmit ultrasonic energy into said object towards said internal structural design feature to generate reflected energy at a discontinuity in said internal structural design feature; and
   detecting said reflected energy and generating an inspection signal representative of a discontinuity in said internal structural design feature.

19. The method of claim 18 including
   transmitting said ultrasonic energy into said object by scanning said ultrasonic energy back and forth across said path on said object.

20. The method of claim 18 including
   filtering false inspection signals by comparing said inspection signals with said position signals.

* * * * *